(12) United States Patent
Boonstra et al.

(10) Patent No.: US 8,399,705 B2
(45) Date of Patent: Mar. 19, 2013

(54) ALKALI METAL SALT OF GLUTAMIC ACID N,N-DIACETIC ACID, A PROCESS TO PREPARE SUCH SALT, AND THE USE THEREOF

(75) Inventors: Tjerk Oedse Boonstra, Duiven (NL); Martin Heus, Arnhem (NL)

(73) Assignee: Akzo Nobel N.V., Arnhem (NL)

( * ) Notice: Subject to any disclaimer, the term of this patent is extended or adjusted under 35 U.S.C. 154(b) by 152 days.

(21) Appl. No.: 12/673,671

(22) PCT Filed: Aug. 14, 2008

(86) PCT No.: PCT/EP2008/060655
§ 371 (c)(1),
(2), (4) Date: Apr. 26, 2010

(87) PCT Pub. No.: WO2009/024518
PCT Pub. Date: Feb. 26, 2009

(65) Prior Publication Data
US 2010/0324334 A1    Dec. 23, 2010

Related U.S. Application Data

(60) Provisional application No. 60/968,432, filed on Aug. 28, 2007.

(30) Foreign Application Priority Data

Aug. 17, 2007 (EP) ..................................... 07114558

(51) Int. Cl.
*C07C 229/24* (2006.01)
(52) U.S. Cl. ..................................................... 562/571
(58) Field of Classification Search .......................... None
See application file for complete search history.

(56) References Cited

U.S. PATENT DOCUMENTS
2008/0300159 A1   12/2008  Seebeck et al.

FOREIGN PATENT DOCUMENTS

| EP | 0 783 034 | 7/1997 |
| EP | 0 884 381 | 12/1998 |
| EP | 1 004 571 | 5/2000 |
| EP | 1 803 801 | 7/2007 |
| JP | 11-092436 | 4/1999 |
| JP | 2000 192091 | 7/2000 |
| JP | 2001 003089 | 1/2001 |
| JP | 2002 356464 | 12/2002 |
| WO | 96/22351 | 7/1996 |

OTHER PUBLICATIONS

International Search Report and Written Opinion, PCT International Application PCT/EP2008/60655, mailed on Jan. 13, 2009.
International Preliminary Report on Patentability, PCT International Application PCT/EP2008/60655, mailed on Feb. 24, 2010.
International Search Report and Written Opinion, PCT International Application PCT/EP2008/60656, mailed on Dec. 19, 2008.
International Preliminary Report on Patentability, PCT International Application PCT/EP2008/60656, dated Dec. 15, 2009.
Jerry March, "Advanced Organic Chemistry," 1992, John Wiley & Sons, XP 002496826, p. 887-888, p. 965, paragraph 6-50, p. 966, paragraph 6-51.
ACR 3242 P1-JP Office Action for Japanese Patent Application No. 2010-520577 dated Sep. 25, 2012.
Chemical Abstract No. 940911-42-2 from CAS Client Services (search date Sep. 11, 2012.
Chemical Abstract No. 940911-41-1 from CAS Client Services (search date Sep. 11, 2012.

*Primary Examiner* — Paul A Zucker
(74) *Attorney, Agent, or Firm* — Timothy D. Meade

(57) ABSTRACT

The present invention relates to an alkalimetal salt of glutamic acid-N,N-diacetic acid (GLDA) of the formula $Na_xK_yH_zGLDA$, wherein x is equal to or more than 2 and lower than 4 and y is more than 0 and equal to or lower than 2, x+y is 3.5-4, and x+y+z=4, to processes to prepare such salt and the use thereof.

35 Claims, 1 Drawing Sheet

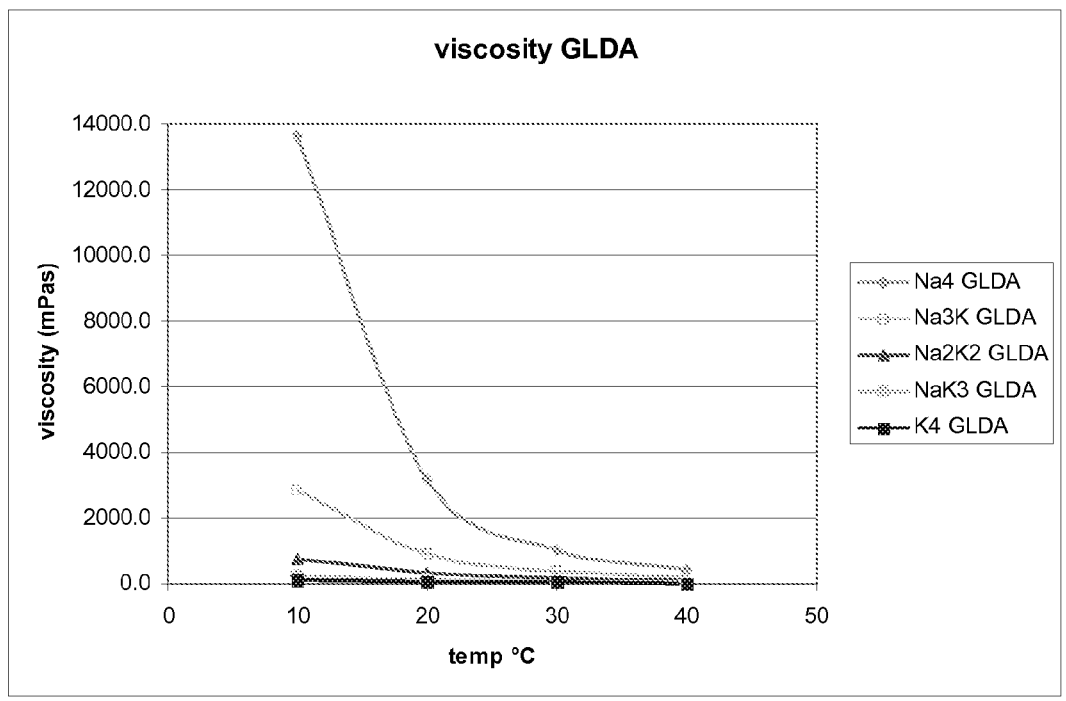
Viscosity determination of 50% $Na_xK_yGLDA$ products in $H_2O$

ALKALI METAL SALT OF GLUTAMIC ACID N,N-DIACETIC ACID, A PROCESS TO PREPARE SUCH SALT, AND THE USE THEREOF

REFERENCE TO RELATED APPLICATION(s)

This application is the U.S. National Phase of PCT/EP20081060655 filed on Aug. 14, 2008 and claims the benefit of U.S. Provisional Application No. 60/968,432 filed on Aug. 28, 2007.

The present invention relates to a group of alkali metal salts of glutamic acid N,N-diacetic acid, a process to prepare them, and the use thereof.

Chelating agents are agents capable of forming a complex with a metal ion. Examples of chelating agents include compounds like EDTA (ethylenediamine N,N,N',N'-tetraacetic acid) and GLDA (glutamic acid, N,N-diacetic acid).

GLDA is disclosed to be useful for a number of applications as it has a good biodegradability and, according to many documents, an alkali metal salt of GLDA is actually applied.

JP 2001-003089 for example discloses a liquid cleaning agent constituent for dish washers having a good biodegradability. As the biodegradable sequestering agent for the cleaning agent tetrasodium salt or tetrapotassium salt of L-glutamic acid acetic acid may be used.

EP 783034 discloses a detergent comprising the tetrasodium salt of glutamic acid-N,N-diacetic acid.

JP 2000192091 discloses a bleaching agent composition that comprises an alkali metal salt of glutamic acid-N,N-diacetic acid.

WO 96/22351 discloses a biocidal composition comprising sodium salt of glutamic acid-N,N-diacetic acid.

JP2002356464 discloses the preparation of highly pure glutamic acid-N,N-diacetic acid by converting the tetrasodium or tetrapotassium salt to the full acid.

EP 1004571 discloses the preparation of glutamic acid-N,N-diacetic acid starting from the tetrasodium salt thereof.

BRIEF DESCRIPTION OF THE DRAWINGS

FIG. 1 shows the viscosity of the products prepared in Examples 1a-e.

In many applications in which GLDA is used high concentrations or even solids are frequently preferred. Not only is this economical (lower transport costs), what is also important is that the active ingredient concentration can be higher without experiencing handling problems such as viscosity, it also leaves more "room" in formulations for other additives such as caustic, surfactants, etc.

However, in practice there are limits to increasing the chelate concentration because the solubility is limited or the viscosity becomes too high. Too highly concentrated products may start to crystallize or they may become too viscous to be handled. In the case of highly concentrated GLDA tetrasodium solutions, viscosity is the main concern.

We have found that the potassium salts of glutamic acid-N,N-diacetic acid have a lower viscosity than the sodium salts thereof. However, to prepare potassium salts a potassium source is needed, which generally is less readily available on a production site and of significantly higher price than the corresponding sodium-containing compound. Many industries have sodium hydroxide on their production sites while potassium hydroxide is less readily available. Another disadvantage is that potassium has a higher atomic weight than sodium, which makes a potassium salt of GLDA weigh more than a sodium salt thereof or, in other words, less chelate is present per kilogram of potassium salt of GLDA than per kilogram of sodium salt of GLDA.

The present invention now provides an alkalimetal salt of glutamic acid-N,N-diacetic acid (GLDA) of the formula $Na_xK_yH_zGLDA$, wherein x is equal to or more than 2 and lower than 4 and y is more than 0 and equal to or lower than 2, x+y is 3.5-4, and x+y+z=4.

The alkalimetal salt of the invention strikes a good balance between low viscosity and being obtainable by a process using raw materials that are easily available on an industrial site for a low price. Also, the alkalimetal salt of the invention has a reasonable molecular weight to viscosity balance, i.e. it has a sufficiently low viscosity to make it transportable and a sufficiently low molecular weight to get sufficient chelate activity per weight unit of alkalimetal chelate salt.

Compared to the full acid of GLDA or the tetrasodium salt of GLDA, the salt of the invention has the benefit that it can be transported in high concentrations (60% expressed in wt % is no problem) while still having a sufficiently low viscosity to be pumpable at low temperatures (<40° C.). This also means that a smaller amount of material needs to be transported to get the same amount of chelate at the place of destination.

Other advantages of the mixed salt are that the solids content of a mixed GLDA salt solution is lower than for a full potassium version for solutions having the same chelating power. The molecular weight of the tetrasodium salt of GLDA, being 351.1, would become 415.1 for the tetrapotassium salt. So to get the same active ingredient with respect to sequestering power almost 20% more material would need to be dissolved. The monopotassium trisodium GLDA of the invention requires only 5% more product to be dissolved instead of 20%, and this without the product having the negative effect of high viscosity at more concentrated solutions when compared with the tetrasodium version, as demonstrated by the Examples.

Preferably, in the alkalimetal salt of GLDA of the invention x is between 2.5 and 3.5 and y is between 0.5 and 1.5, most preferably x is about 3 and y is about 1.

In one embodiment the invention provides a process to prepare the above alkalimetal salt of glutamic acid-N,N-diacetic acid (GLDA) of the formula $Na_xK_yH_zGLDA$ wherein x is equal to or more than 2 and lower than 4 and y is more than 0 and equal to or lower than 2, x+y is 3.5-4, and x+y+z=4, comprising reacting glutamic acid, a sodium or potassium salt thereof or a mixture thereof, with formaldehyde, hydrogen cyanide, a potassium or sodium salt thereof or a mixture thereof, and potassium hydroxide, sodium hydroxide or a mixture thereof, in an aqueous solution at an elevated temperature to remove formed $NH_3$, characterized in that during the process the molar ratio of sodium to potassium in the reactants is between 1:1 and 7:1.

Preferably, the molar ratio of sodium to potassium in the reactants is between 2:1 and 4:1, most preferably about 3:1.

In this embodiment the novel group of glutamic acid-N,N-diacetic acid salts is prepared by a so-called Strecker/Bersworth route at alkaline conditions using an 1-pot synthesis. The reaction route encompasses reacting glutamic acid with formaldehyde and hydrogen cyanide in the presence of sodium hydroxide and potassium hydroxide. The excess cyanide/formaldehyde needed is 10% or more; use is made of a minimum of 2.2 equivalents cyanide/formaldehyde per equivalent of glutamic acid.

The individual dosing of formaldehyde and HCN can also be combined to generate glycolonitrile (HO—$CH_2$—CN). This glycolonitrile is reacted with glutamic acid or the sodium or potassium salt thereof in an alkaline environment (Strecker/Bersworth process).

1 glutamic acid+2HO—CH$_2$—CN+3NaOH+1 KOH→GLDA-KNa$_3$+2 NH$_3$+2H$_2$O

Preferably, the alkalimetal salts of the invention are prepared by a Singer process comprising two or more steps, wherein in a first step a glutamic acid, a sodium or potassium salt thereof or a mixture thereof is reacted with formaldehyde and hydrogen cyanide, at a pH equal to or below 7, and in a subsequent step the nitrile compound formed in the first step is hydrolyzed with sodium hydroxide, potassium hydroxide or a mixture thereof, characterized in that the molar ratio of sodium to potassium in the reactants is between 1:1 and 7:1.

In a more preferred embodiment, a two-step process in which the first step takes place at neutral or acidic pH (the above so-called Singer process), between 1.6 and 2.4 equivalents of formaldehyde are used per equivalent of glutamic acid or salt thereof and 1.6 to 2.4 equivalents of HCN are used per equivalent of glutamic acid or salt thereof. In an even more preferred embodiment 1.9-2.1 equivalents of formaldehyde and HCN are used per equivalent of glutamic acid or salt thereof. Most preferably, the amount of formaldehyde and HCN is about 2.0 equivalents per equivalent of glutamic acid or salt thereof. In the process the amount of HCN may be (but does not need to be) the same as the amount of formaldehyde.

The overall reaction (for example trisodium monopotassium salt, x=3, y=1) is:

1 glutamic acid+2CH$_2$O+2HCN+3NaOH+ 1KOH→GLDA-KNa$_3$+2NH$_3$+2H$_2$O

It will be clear that instead of starting with glutamic acid, it is possible to use sodium or potassium glutamate. The same holds for hydrogen cyanide and sodium hydroxide; sodium cyanide, potassium cyanide, and potassium hydroxide are alternatives.

In a more preferred embodiment the first step is split up into two substeps, firstly a reaction of glutamic acid or glutamate with formaldehyde to generate a Schiff base intermediate and subsequently a reaction with HCN and further formaldehyde to form a nitrile.

In the above preferred process the raw material is monosodium glutamate, glutamic acid or monopotassium glutamate. The very low solubility of glutamic acid can be overcome by dissolving it in NaOH or KOH (resulting in the formation of monosodium or monopotassium glutamate); having about 0.6-1.4 equivalents of base is preferred. In the manufacturing of GLDA the monosodium salt or monopotassium salt of glutamic acid is dissolved in water and formaldehyde and cyanide are added under acidic or neutral conditions.

In the case of synthesis of the intermediate nitrile the addition of formaldehyde and hydrogen cyanide preferably takes place at a temperature between 10 and 40° C. The result is an intermediate product having two nitrile functionalities. These types of products are known as aminoacetonitriles or, for short, "nitriles". The nitrile of GLDA, e.g. potassium or sodium glutamate diacetonitrile, is also indicated as GLDN below. The nitrile, being extremely water-soluble, is hydrolyzed in a second step applying caustic.

The overall reaction will be:

HOOC—CH$_2$—CH$_2$—C(H)(COOM')—N—(CH$_2$—CN)$_2$+3M(OH)+1H$_2$O→MOOC—CH$_2$—CH$_2$—C(H)(COOM')—N—(CH$_2$—COOM)$_2$+2NH$_3$ (aminoacetonitriles intermediate+base→aminocarboxylate+ ammonia)

In the above reaction each M and M' may be the same or different and represent an alkalimetal ion.

The process has as an additional benefit that having potassium GLDN one needs only sodium hydroxide to produce the GLDA-KNa$_3$. Not all production locations have access to KOH or storage tanks of KOH; NaOH is more commonly used. Production of a mixed salt is easier than of the full potassium version that requires KOH to be present in each location, i.e. the location carrying out the nitrile hydrolysis only needs the commonly used NaOH.

Accordingly, a process is provided wherein in the first step the glutamic acid diacetonitrile monopotassium salt is formed by reacting either potassium glutamate with hydrogen cyanide and formaldehyde or glutamic acid with potassium cyanide and formaldehyde, the nitrile being hydrolyzed with sodium hydroxide in the subsequent step.

As starting material instead of glutamic acid also the potassium salt thereof can be employed. The main advantage of monopotassium glutamate in the production process is its very high solubility even at room temperature. Monosodium glutamic acid (MSG) has a solubility of ~40 wt % in water at room temperature, monopotassium glutamate has a solubility of ~65-70 wt % The more concentrated the glutamate can be processed, the less water removal is required to make a concentrated GLDA solution. The monosodium GLDN (=glutamic acid amino diacetonitrile monosodium salt) manufactured has a concentration related to the maximum achievable concentration of the monosodium glutamate and the amount of water added by using aqueous formaldehyde. It will be clear that the use of concentrated formaldehyde solutions is advantageous.

In the case of the potassium version of GLDN, the final nitrile concentration will be higher due to the high solubility of potassium glutamate. It allows for more economical transport, more output per reactor volume, lower energy costs, and is an easy way to produce highly concentrated final GLDA solutions in the hydrolysis of the nitrile functionalities without water removal.

It is possible to produce and isolate an amide (which is a partially hydrolyzed nitrile). Storage of GLDN for a longer period of time at a pH that is slightly acidic/-neutral is found to trigger hydrolysis, but because the hydrolysis conditions are mild the hydrolysis will not be complete, resulting in the formation of a mono- or di-amide functionality instead of a carboxylate acid functionality. It will be clear that these amides when precipitated and isolated can be used to synthesize highly pure GLDA solutions substantially free of by-products, by means of further hydrolysis.

Hence in one embodiment the invention provides a process to prepare the alkali metal salt of GLDA wherein hydrolysis takes place in two steps, the first at a pH between 0.5 and 7, preferably between 2.5 and 7, to give glutamic acid-N,N-diacetic amide, glutamic acid-N-monoacetic amide-N-monoacetonitrile or the potassium or sodium salt thereof, and a subsequent step at a temperature of at least 90° C. and an alkaline pH to give glutamic acid-N,N-diacetic acid or the sodium or potassium salt thereof, the process optionally comprising an additional intermediate step of isolating the glutamic acid-N,N-diacetic amide, glutamic acid N-monoacetic amide N-monoacetonitrile or the potassium or sodium salt thereof.

These amide intermediates are represented by the structures:
HOOC—CH$_2$—CH$_2$—CH(COOM)-N—(CH$_2$—CN)(CH$_2$—C(O)—NH$_2$) for the monoamide-mononitrile, or
HOOC—CH$_2$—CH$_2$—CH(COOM)-N—(CH$_2$—C(O)—NH$_2$)$_2$ for the diamide, wherein M=K, Na or H.

To be able to make specific Na$_x$K$_y$H$_z$GLDA salts of the invention, a process wherein the ratio between x and y can be easily fine-tuned is also desired.

Therefore the invention provides the following two alternative processes. Firstly, a process comprising titrating glutamic acid-N,N-diacetic acid (or an appropriate derivative or salt thereof) with a sodium salt and a potassium salt wherein the molar ratio of sodium to potassium in the materials is between 7:1 and 1:1 and, secondly, a process of mixing the tetrasodium salt of GLDA and the tetrapotassium salt of GLDA in a molar ratio of between 7:1 and 1:1.

Finally, the present invention relates to the use of the alkalimetal salts in a detergent composition, a descaling composition, a microbial composition, an oil well stimulating composition, a micronutrient composition, in gas sweetening, pulp and paper bleaching, or in the preparation of any of such compositions.

EXAMPLES

Examples 1a and b, Comparative Examples 1c-e

Different $Na_xK_y$GLDA products were prepared by mixing the following raw materials:
GLDA-$H_4$ (made from Dissolvine GL-45-S ex Akzo Nobel NV ion exchanged with a strong acidic resin to generate GLDA-$H_4$), 50% NaOH in aqueous solution, 45% KOH in aqueous solution, in accordance with Table 1 below.

TABLE 1

Preparation of several $Na_xK_y$GLDA products

| Example | Product | Reactants |
|---|---|---|
| 1a | $Na_3$KGLDA | 1 eq GLDA $H_4$ + 3 eq NaOH (50% sol) + 1 eq KOH (45% sol) |
| 1b | $Na_2K_2$GLDA | 1 eq GLDA $H_4$ + 2 eq NaOH (50% sol) + 2 eq KOH (45% sol) |
| 1c (comp.) | $NaK_3$GLDA | 1 eq GLDA $H_4$ + 1 eq NaOH (50% sol) + 3 eq KOH (45% sol) |
| 1d (comp.) | $K_4$GLDA | 1 eq GLDA $H_4$ + 4 eq KOH(45% sol) |
| 1e (comp.) | $Na_4$GLDA | 1 eq GLDA $H_4$ + 4 eq NaOH (50% sol) |

After addition of the KOH (45% sol) and the NaOH (50% sol) solution the products were subjected to evaporation to isolate an alkalimetal salt of glutamic acid-N,N-diacetic acid product having a concentration of 50 wt %.

The viscosity of the alkalimetal salt of glutamic acid-N,N-diacetic acid products prepared in Examples 1a-e was determined using a Brookfield DV-II viscometer with a spindle 34 at a temperature of 10 to 40° C. The results are given in FIG. 1.

This measurement demonstrates the significantly lower viscosity of $Na_3$K GLDA and $Na_2K_2$ GLDA compared to $Na_4$ GLDA.

Example 2a $Na_3K_2$GLDA was prepared using the following preparation process:
222 kg glutamic acid (ex Fluka) were dissolved in 182 kg potassium hydroxide 46.3 wt % (one equivalent KOH) at a temperature below 60° C. to yield a homogeneous solution of 404 kg monopotassium glutamic acid (~70 wt % in $H_2O$).

After the solution was cooled to room temperature, 102 kg of a ~44 wt % formaldehyde solution were dosed (1 equivalent) to give the so-called Schiff-base in a clear solution.

To a reactor pre-charged with this solution, 102 kg ~44 wt % formaldehyde solution (another equivalent) and 81 kg of HCN (2 equivalents) were simultaneously dosed applying the usual safety conditions. During this simultaneous dosing the temperature was kept below 40° C. by continuously cooling the reaction mixture. After the addition of formaldehyde and hydrogen cyanide was complete, the reaction mixture was stirred for at least 30 minutes. The reaction mixture contained about 57 wt % potassium glutamate diacetonitrile.

In a second step hydrolysis took place. A reactor was pre-charged with 140 kg of water and 60 kg 50 wt % aqueous NaOH solution and this mixture was heated to 90-100° C. Subsequently, 322 kg of 50% NaOH solution and the entire glutamic acid diacetonitrile monopotassium salt mixture resulting from the previous reaction step were simultaneously dosed to this heated solution in about 90 minutes. After the dosing was completed, the reaction mixture was boiled under the removal of ammonia and water. The boiling was stopped when almost all ammonia generated by the saponification had been removed and the appropriate GLDA salt concentration reached (~70 wt % in $H_2O$). The solution was cooled to room temperature, allowing storage or further processing. Analysis by NMR and AAS showed that the product was monopotassium trisodium glutamic acid-N,N-diacetic acid with a yield of over 90% based on glutamic acid.

Comparative Example 2b

For the preparation of the tetrasodium salt of GLDA, the procedure of Example 2a was repeated, except that in the first reaction step 120 kg 50 wt % (one equivalent) aqueous NaOH were used to dissolve the sodium salt of glutamic acid (MSG). The solubility of MSG is more limited than that of the potassium salt of glutamic acid (MPG) and as a consequence the nitrile solution is more diluted. The final product, $Na_4$ GLDA, was isolated in a concentration of ~55 wt % in $H_2O$ and analysis by NMR and AAS showed that the product was tetrasodium glutamic acid-N,N-diacetic acid with a yield of over 90% based on glutamic acid.

Example 3

222 kg glutamic acid (ex Fluka) were dissolved in 182 kg potassium hydroxide 46.3 wt % (one equivalent KOH) at a temperature below 80° C. to yield a homogeneous solution of 404 kg monopotassium glutamic acid (~70 wt % in $H_2O$). To this solution 1 equivalent of 50 wt % NaOH was added. The temperature of the glutamate solution was raised to boiling point and 2.2 equivalents of NaCN 30 wt % (539 kg) and 2.2 equivalents of formaldehyde 44 wt % (229 kg) were simultaneously dosed while keeping the solution at its boiling point. The solution was heated to boiling for several hours. Ammonia was released and $KNa_3$ GLDA was formed, as confirmed by NMR and AAS analyses.

Example 4

222 kg glutamic acid (ex Fluka) were dissolved in a mixture of with 182 kg potassium hydroxide 46.3 wt % (one equivalent KOH) and 360 kg NaOH 50 wt % (3 equivalents). When the dissolution was complete 89 kg HCN (2.2 eq.) and 229 kg 44 wt % formaldehyde (2.2 eq.) were simultaneously dosed. The solution was heated to boiling for several hours. Ammonia was released and $KNa_3$ GLDA formed.

Example 5

Mixing of $Na_4$ GLDA and $K_4$ GLDA in a molar ratio 3:1
234 kg of a 45 wt % solution of tetrasodium GLDA were mixed with 75.5 kg of a 55 wt % solution of tetrapotassium GLDA to obtain 309.5 kg of a 47.7 wt % solution of $KNa_3$GLDA.

The invention claimed is:

1. A process to prepare an alkalimetal salt of glutamic acid-N,N-diacetic acid (GLDA) of the formula $Na_xK_yH_zGLDA$, wherein x is equal to or more than 2 and lower than 4 and y is more than 0 and equal to or lower than 2, x+y is 3.5-4, and x+y+z=4, comprising reacting glutamic acid, a sodium or potassium salt thereof or a mixture thereof with formaldehyde, hydrogen cyanide, a potassium or sodium salt thereof or a mixture thereof and potassium hydroxide, sodium hydroxide or a mixture thereof, in an aqueous solution at an elevated temperature to remove formed $NH_3$, wherein during the process the molar ratio of sodium to potassium in the reactants is between 1:1 and 7:1.

2. The process of claim 1 wherein x is about 3 and y is about 1.

3. The process of claim 1 wherein x is between 2.5 and 3.5 and y is between 0.5 and 1.5.

4. A process to prepare an alkalimetal salt of glutamic acid-N,N-diacetic acid (GLDA) of the formula $Na_xK_yH_zGLDA$, wherein x is equal to or more than 2 and lower than 4 and y is more than 0 and equal to or lower than 2, x+y is 3.5-4, and x+y+z=4, comprising two or more steps, wherein in a first step glutamic acid, a sodium or potassium salt thereof or a mixture thereof is reacted with formaldehyde and hydrogen cyanide, at a pH equal to or below 7, and in a subsequent step the nitrile compound formed in the first step is hydrolyzed with sodium hydroxide, potassium hydroxide or a mixture thereof, wherein the molar ratio of sodium to potassium in the reactants is between 1:1 and 7:1.

5. The process of claim 4 wherein in the first step the glutamic acid diacetonitrile monopotassium salt is formed by reacting either potassium glutamate with hydrogen cyanide and formaldehyde or glutamic acid with potassium cyanide and formaldehyde, the nitrile being hydrolyzed with sodium hydroxide in the subsequent step.

6. The process of claim 4 wherein the hydrolysis takes place in two steps, a first step at a pH between 0.5 and 7 to give glutamic acid-N,N-diacetic amide, glutamic acid-N-monoacetic amide-N-monoacetonitrile or the potassium or sodium salt thereof, and a subsequent step at a temperature of at least 90° C. and an alkaline pH to give glutamic acid-N,N-diacetic acid or the sodium or potassium salt thereof, the process optionally comprising an additional intermediate step of isolating the glutamic acid-N,N-diacetic amide.

7. A process to prepare an alkalimetal salt of glutamic acid-N,N-diacetic acid (GLDA) of the formula $Na_xK_yH_zGLDA$, wherein x is equal to or more than 2 and lower than 4 and y is more than 0 and equal to or lower than 2, x+y is 3.5-4, and x+y+z=4, comprising titrating glutamic acid-N,N-diacetic acid with a sodium salt and a potassium salt, wherein the molar ratio of sodium to potassium in the materials is between 7:1 and 1:1.

8. A process to prepare an alkalimetal salt of glutamic acid-N,N-diacetic acid (GLDA) of the formula $Na_xK_yH_zGLDA$, wherein x is equal to or more than 2 and lower than 4 and y is more than 0 and equal to or lower than 2, x+y is 3.5-4, and x+y+z=4, comprising mixing the tetrasodium salt of GLDA and the tetrapotassium salt of GLDA in a molar ratio of between 7:1 and 1:1.

9. The process of claim 1 wherein the molar ratio of sodium to potassium is between 1:1 and 4:1.

10. The process of claim 1 wherein the potassium or sodium hydroxide is used in an excess.

11. The process of claim 4 wherein the molar ratio of sodium to potassium is between 1:1 and 4:1.

12. The process of claim 4 wherein the potassium or sodium hydroxide is used in an excess.

13. An alkalimetal salt of glutamic acid-N,N-diacetic acid (GLDA) of the formula $Na_xK_yH_zGLDA$, wherein x on average is equal to or more than 2 and lower than 3.5 and y on average is more than 0.5 and equal to or lower than 2, x+y is 3.5-4, and x+y+z=4.

14. An oil well composition comprising the alkalimetal salt of claim 13.

15. A detergent composition comprising the alkalimetal salt of claim 13.

16. A descaling composition comprising the alkalimetal salt of claim 13.

17. A microbial composition comprising the alkalimetal salt of claim 13.

18. A micronutrient composition comprising the alkalimetal salt of claim 13.

19. A gas sweetening composition comprising the alkalimetal salt of claim 13.

20. A pulp and paper bleaching composition comprising the alkalimetal salt of claim 13.

21. The alkalimetal salt of claim 13 wherein x on average is between 2.5 and 3.5 and y on average is between 0.5 and 1.5.

22. The alkalimetal salt of claim 13 wherein x on average is about 3 and y on average is about 1.

23. An aqueous solution comprising an alkalimetal salt of glutamic acid-N,N-diacetic acid (GLDA) of the formula $Na_xK_yH_zGLDA$, wherein x on average is equal to or more than 2 and lower than 4 and y on average is more than 0 and equal to or lower than 2, x+y is 3.5-4, and x+y+z=4.

24. The aqueous solution of claim 23 wherein x on average is between 2.5 and 3.5 and y on average is between 0.5 and 1.5.

25. The aqueous solution of claim 23 wherein x on average is about 3 and y on average is about 1.

26. The process of claim 4 wherein x is between 2.5 and 3.5 and y is between 0.5 and 1.5.

27. The process of claim 4 wherein x is about 3 and y is about 1.

28. The process of claim 7 wherein x is between 2.5 and 3.5 and y is between 0.5 and 1.5.

29. The process of claim 7 wherein x is about 3 and y is about 1.

30. The process of claim 9 wherein x is between 2.5 and 3.5 and y is between 0.5 and 1.5.

31. The process of claim 8 wherein x is about 3 and y is about 1.

32. An alkalimetal salt prepared by the process of claim 1.

33. An alkalimetal salt prepared by the process of claim 4.

34. An alkalimetal salt prepared by the process of claim 7.

35. An alkalimetal salt prepared by the process of claim 8.

* * * * *